ary Examiner—Norman Yudkoff
United States Patent [19]
Kawano et al.

[11] 3,939,279
[45] Feb. 17, 1976

[54] FEED AND METHOD OF AQUIANIMALS CULTIVATION

[75] Inventors: Takatsugu Kawano; Hiroshige Kojima; Hiroshi Ohosawa; Kazuto Morinaga, all of Nobeoka, Japan

[73] Assignee: Asahi Kasei Kogyo Kabushiki Kaisha, Osaka, Japan

[22] Filed: June 27, 1973

[21] Appl. No.: 373,910

Related U.S. Application Data

[63] Continuation-in-part of Ser. No. 66,575, Aug. 24, 1970, abandoned.

[30] Foreign Application Priority Data

Aug. 22, 1969 Japan.................................. 44-65961

[52] U.S. Cl. ........................ 426/2; 426/62; 426/60; 195/91
[51] Int. Cl.² ........................................... A23L 1/28
[58] Field of Search ........ 195/82, 85, 91, 92; 119/2, 119/3, 5, 51; 426/2, 62, 204, 805, 53, 54, 60

[56] References Cited
UNITED STATES PATENTS

3,576,643   4/1971   Ayvkawa ................................... 99/2
3,830,937   8/1974   Shigeno ................................. 426/62

FOREIGN PATENTS OR APPLICATIONS

558,668   6/1958   Canada ..................................... 99/9
2,059,114   5/1971   France .................................... 426/62

*Primary Examiner*—Norman Yudkoff
*Assistant Examiner*—Hiram H. Bernstein
*Attorney, Agent, or Firm*—Cooper, Dunham, Clark, Griffin & Moran

[57] ABSTRACT

A feed comprising a culture product of strains of marine or halophilic yeasts in which the COD rising index of the strain is not more than 150 and the RNA excretion rate is not more than 20% in a medium containing waste molasses and an inorganic nitrogen compound, and a method for cultivating aquianimals with the feed. Typical example of the yeasts is Torulopsis candida var. marina NRRL Y-7345. The feed is particularly useful for breeding, for example, Brachionus, Copepoda, Brine Shrimp and Stage of Zoea, Mysis and Post Larva of shrimps.

13 Claims, No Drawings

FEED AND METHOD OF AQUIANIMALS CULTIVATION

This application is a continuation-in-part application of United States Application Ser. No. 66,575 filed Aug. 24, 1970 and now abandoned.

This invention relates to feed for useful aquianimals and a cultivation of the aquianimals. More particularly, the invention pertains to a method for efficiently breeding and culturing fish, shellfish and zooplankton, which comprises culturing a specific strain of microorganism in a medium containing waste molasses and an inorganic nitrogen compound as sources of carbon and nitrogen, respectively. The strain is selected from marine or halophilic yeasts having defined sucrose-assimilating ability and defined secreting ability of endo (intercell)-effective substances into sea water. The measure of said secreting ability is based on Chemical Oxygen Demand (hereinafter referred to as "COD" rising index) with respect to participating substances and Ribonucleic acid excretion rate (hereinafter referred to as "RNA" excretion rate). Yeast strains used in this invention have a COD rising index which is not more than 150 and an RNA excretion rate which is not more than 20%.

Recently, the cultivation of fish has become an important industry and food source. A problem of great significance in connection with the cultivation of fish on a large scale is the provision of a nutritionally adequate, inexpensive food for the growing fish, especially in the early stages of growth.

Conventionally, in breeding fish and shellfish, especially spawns, seeds and seedlings, they are first fed with phytoplankton and, as the case may be, with Diatoms, Chlorophyta and the like. They may be later fed with zooplankton as growth progresses and their nutritional requirements change.

It is necessary, in order to provide a sufficient concentration of zooplankton for utilization by the growing spawns, seeds and seedlings, to provide an adequate feed for the zooplankton. Such feeds as have been heretofor available have not been completely satisfactory and therefore there have been considerable efforts at improvement.

In previous attempts to provide adequate nutrition various yeasts such as those used in the production of beer, yeasts living in the drainage of pulp manufacturing plants, hydrocarbon assimilating yeasts and various other types of yeasts have been recommended. They have been unsatisfactory, however, for a number of reasons. For example, they may not multiply quickly enough to provide sufficient feed, they may be nutritionally inadequate for the growing fish and crustacea larvae, or they may pollute the breeding medium by elution of intracellular factors into the medium. This last mentioned problem is especially troublesome when zooplankton and phytoplankton are combined for use as feeds.

It has now been discovered, in accordance with the invention, that certain strains of marine and halophilic yeasts are an excellent feed source for use in the cultivation of aquianimals, i.e. fish and crustacea. The strains of yeast which are useful in this invention are free of toxins for the growing larvae and have a COD rising index which is not more than 150 and an RNA excretion rate which is not more than 20%. By using yeasts having these properties, it is possible not only to obtain a marked effect in preventing pollution of the breeding medium but also to stabilize and maintain various physical and chemical conditions of the environment of the medium. Not all strains of a particular species are useful in the practice of this invention.

The microorganisms used in the present invention are yeasts which are widely distributed in the seas. The most practically useful yeasts are those having sucrose-assimilating ability coupled with a high yield based on carbon sources in the culture medium. Conventionally known marine yeasts are very slow in their growth. Except for yeasts belonging to genus Zygosaccharomyces with which glucose is used, there has been no report of strains belonging to any genera in which the growth rate of cells exceeds 1 g/dl.

It has been observed that yeasts having the properties described above do not excrete cellular substances into the breeding medium in sufficient quantities so that pollution becomes a problem. The presence of absence of toxins can be readily determined by simple observation of a few growth systems. For example, a zooplankton of small size may be fed a selected yeast for a short period of time, e.g. one week, and the rate of growth observed. Nauplius of Brine Shrimp (*Artemia salina*) are suitable for these determinations.

Typical examples of the strains of yeasts usuable in the present invention are shown in Table 1. These strains have been deposited in Fermentation Research Institute, Agency of Industrial Science and Technology, Chiba City, Japan, under BIKOOKENKINKI Nos. 346, 347, 348, 349 and 350, respectively. The have also been deposited at the United States Department of Agriculture, Northern Utilization Research and Develoopment Division at Peoria, Illinois under the deposit numbers NRRL Y-7345, NRRL Y-7346, NRRL Y-7347, NRRL Y-7348 and NRRL Y-7349, respectively.

Among these strains, No. 346 belongs to genus Cryptococcaceae because it has non-ascospore. Because of having no arthrospore and showing no carotinoid color formation, it does not belong to genera Trichosporon and Rodotorula. No pseudomycelium and mycelium are recognized, and hence, it does not belong to genus Candida. Neither both pole budding nor triangular cells are observed therein. As there is no production of strong acid, and production of starch is (−), this strain is considered to be one of species belonging to genus Torulopsis. From assimilation of sucrose and utilization of nitrate, the strain is analogus to strain of Torulopsis candida. Moreover, taking account of its chlorine resistance, No. 346 strain has been identified as "*Torulopsis candida* var. marina".

No. 347 is characterized by a spore of small size, and is close to strains of Saccharomyces mellis. They are, however, markedly different in sucrose-assimilating ability from each other. Accordingly, No. 347 is a new species and has been named "Saccharomyces disaccharomellis".

No. 348 strain belongs to genus Rhodotorula, in view of the fact that it does not form ascospore and has no arthrospore but has carotinois color-forming ability. Furthermore, it neither shows essential vitamin-requiring property nor has lactose-assimilating ability. This strain is considered to be close to the strain of *Rhodotorula rubra*, but they are different from each other in the temperature limits for growth and sucroseassimilating ability. Accordingly, No. 348 strain has been named as "*Rhodotorula rubra* var. marina".

No. 349 buds and thereby grows. From glucose-fermentating ability, form of spore, fermentation rate, cell size and binary spore form, it is close to strains of *Saccharomyces acidifaciens* and *Saccharomyces halomembranis*. However, in view of the sucrose-assimilating abilities of these two strains, No. 349 differs from them. It has been named "*Saccharomyces acidosaccharophillii*" as a new species.

No. 350 is a strain similar to No. 346, but it is (−) with respect to assimilation of lactose. This strain also resembles *Torulopsis famata*, but is different therefrom in fermentive action on glucose, growth in a culture medium of high sodium chloride concentration, culture on a litmus milk medium and sugar assimilation. Accordingly, No. 350 is named "*Torulopsis larvae*", a new species.

The above identification is based on:

1. "Tanpakushitsu, Kakusan, Koso" ("Protein, Nucleic acid and Enzyme"), Vol. 12, No. 3, pp. 256–258 and 346–352,
2. "Iden" ("Heredity"), Vol. 22, pp. 51–56,
3. "Rinshio Kensa" ("Clincial Examination"), Vol. 10, No. 2, pp. 38–44 and No. 3, pp. 34–40, and
4. "Nippon Kinruishi" ("Magazine on fungi and mould fungus in Japan") Vol. 3, Ascomycetes.

Those having bacteriological and physiological characteristics mentioned above are examples of the yeasts usuable in the present invention.

The excretion into a breeding medium of endo (intercell)-effective substances is determined based on the measurement of the amount of substances produced which participate in the COD and RNA respectively in "artifical sea water". For this determination, yeast cells are suspended in artificial sea water adjusted to pH 8 in the proportion of 1 g/dl, at 30°±0.5°C under milk agitation so that the cells do not precipitate. After 48-hours' operation, amounts of COD participating substances and RNA present in the supernatant and in the whole suspension are assayed according to standard methods. "COD rising index" and "RNA excretion rate" as referred to herein are the numerical values obtained in such measurements. Numerical values actually determined with respect to the present strains and controls (baker's yeast and hydrocarbon-assimilating yeast) are shown in Table 1. It is clear from the results shown in the table that yeasts useful in the invention because they have the defined COD and RNA do not pollute the breeding medium to the same extent as the control products which do not have the required COD and RNA properties.

It has been further observed that stabilization of environmental conditions as mentioned above may be more readily observed by using algae in combination with the yeasts of the invention.

The bacteriological characteristics of certain of the yeast strains which can be used in this invention are shown in Table 2.

Table 1

| Strain | COD Rising Index* | RNA Excretion Rate** | Degree of Pollution by Bacteria*** |
|---|---|---|---|
| *Candida petrophilum* | 295 | 34.20 | $4.5 \times 10^7$ cells/ml |
| Baker's yeast | 580 | 52.41 | $2.3 \times 10^7$ |
| Marine yeast ASY-4011 (BIKOOKENKINKI No. 346) | 124 | 3.57 | $1.2 \times 10^7$ |
| " ASY-4021 (BIKOOKENKINKI No. 347) | 108 | 3.30 | $0.4 \times 10^7$ |
| " ASY-4031 (BIKOOKENKINKI No. 348) | 131 | 4.35 | $0.5 \times 10^7$ |
| " ASY-4041 (BIKOOKENKINKI No. 349) | 119 | 3.14 | $0.7 \times 10^7$ |
| " ASY-4051 (BIKOOKENKINKI No. 350) | 110 | 2.85 | $0.9 \times 10^7$ |
| *Zygosaccharomyces marinus* (*Saccharomyces marinus*) | 255 | 28.51 | $2.1 \times 10^7$ |

*Based on an initial value of 100.
**(Eluted RNA/RNA initially contained in cell) × 100.
***Value is cells/ml 48 hours after initiation of the test.

Table 2

| Feature \ Strain | BIKOOKENKINKI No. 346 | BIKOOKENKINKI No. 347 | BIKOOKENKINKI No. 348 | BIKOOKENKINKI No. 349 | BIKOOKENKINKI No. 350 |
|---|---|---|---|---|---|
| Microscopic observation | Spherical or short-egg shape. No Ascospore formation. | Egg and long egg shapes. Ascospore formed. | Spherical. No Ascospore formation. | Spherical to egg shape. Ascospore formed. | Spherical to egg shapes. No Ascospore formation. |
| Wort culture (sea water) | Ring forming. Uniformly grows. Produces crust. | Ring forming. Uniformly grows. Produces crust. | No ring forming. Produces crust. | Forms yeast ring. Produces crust. Uniformly grows. | No ring forming. Produces crust. |
| Sea water-wort - agar culture (cont'g dextrose) | No luster. Grows satisfactory. Convexed. Smooth surface. Wet. White. | No luster. Grows extremely satisfactory. Convexed. Surface with wrinkles. Dry. Pale yellow. | Luster. Convexed. Grows actively. Smooth surface. Wet. Red. | Luster. Convexed. Smooth surface. Dry. White. | Slight luster. Convexed. Grows actively. Smooth surface. Wet. White. |
| Vitamin-requiring property | None. Grows vigorously in the presence of vitamines | None. | None. Grows vigorously in the presence of vitamines. | None. Grows vigorously in the presence of vitamines. | None. |
| KNO₃-assimilation | Negative | Negative | Negative | Negative | Negative |
| Ethanol-assimilation | Positive but very slight | Negative | Negative | Negative | Negative |

Table 2-continued

| Feature \ Strain | BIKOOKENKINKI No. 346 | BIKOOKENKINKI No. 347 | BIKOOKENKINKI No. 348 | BIKOOKENKINKI No. 349 | BIKOOKENKINKI No. 350 |
|---|---|---|---|---|---|
| Acetic acid-assimilation | Positive | Negative | Positive | Positive | Negative |
| NaCl concentration | Growth even without NaCl. Withstands 7%. | Growth even without NaCl. Withstands 7%. | Growth even without NaCl. Withstands 7%. | Growth even without NaCl. Withstands 7%. | Growth even without NaCl. withstands 7%. |
| Sugar-assimilation and fermentative power. | Assimilates glucose, sucrose, galactose, maltose, lactose and raffinose. Not ferment. | Assimilates glucose, sucrose, galactose, maltose, raffinose and lactose. Ferments only glucose. (48 hours) | Assimilates glucose, galactose and surose, but lactose and raffinose to (−) or (±). Not assimilates maltose. Not ferment. (48 hrs) | Assimilates glucose, galactose maltose and raffinose, but not lactose. Ferments only glucose. (48 hours) | Assimilates glucose, sucrose, maltose and galactose, but lactose and raffinose to (−) or (±). Not ferment. (48 hours) |

In addition to the above-exemplified effective strains of marine yeasts, certain selected strains of terrestrial yeasts are also useful in the invention. Such strains include halophilic yeasts, so-called film forming yeasts. The halophilic yeasts are inferior to marine yeasts in effectiveness, but are much superior to phytoplankton.

The present in a medium of waste molasses and an inorganic nitrogen compound is indispensable for the culture of the present strains. Small amounts of phosphate and potassium in the medium are preferably utilized. Moreover, there is absolutely no necessity for using the expensive nutritional materials conventionally used in the culture of marine yeasts such as polypeptone, yeast extracts and the like. The sugar concentration employed in the culture may be at least 1 g/dl. Some strains withstand sugar having a concentration of about 10 g/dl, and still propagate actively.

The nitrogen source may be ammonia or various urea compounds. Organic nitrogen compounds are not necessary. The concentration of nitrogen source mentioned above may be 100–700 mg/dl.

With a medium containing only the carbon and nitrogen sources above, the desired rate of cell growth may be obtained. It is, however, preferable to utilize small amounts of potassium salts and phosphates in the medium, for example about 5–10 mg/dl.

The simple composition of the culture medium is a special feature of the present invention. No cases of cultivation of marine yeasts under such conditions have been previously reported.

In carrying out the culture, conventional submerged culture systems may be employed. Fermentation tanks made of unalloyed iron are not appropriate for use in the present culture, because the iron would be corroded by the sea water.

The pH value of the present medium is preferably in a range of 4 to 6. The present strains are extremely resistant in sea water to infectious microbes. It is, therefore, possible to sufficiently conduct the desired culture of strain by means of a relatively simple culturing apparatus.

The cells thus obtained by cultivation of the selected strains are used as feeds. The culture liquor may also be used, as it is, for feeding. The latter, however, is poor in preservability. In practice, the cells obtained are preferably separated by means of a yeast separator or similar device. After washing with sea water, the cells in a paste-like state are refrigerated for preservation. Alternatively, they may be formed into pressed yeast, or may be lyophilized and then stored in a cold chamber. Further, they may be dried by heating and then stored in a well ventilated area. When using cells for preparation of a compound feed, they are blended, in the form of a paste or a cake, with such additional component or components as may be desired.

When the cells are used for feeding aquianimals of small size, they may be maintained at such concentration that the turbidity of the cells in the breeding medium may always be confirmed visually, though this may vary depending on the kind of aquianimals to be fed therewith. A colorimeter may be employed for more accurate control, for example, where the control is effected to maintain optical density (−long T = OD) at 610 m$\mu$ in the range of about 0.01 –0.5.

The feeding period is similar to that of phytoplankton feeds used with conventional seeds and seedlings cultivation. This period is especially effective when applied to microcrustaceans.

The present yeasts are effectively used as feeds at the initial stage of breeding seeds and seedlings, such as Brachionus, Copepoda, Brine Shrimp, and fry of various kinds of shrimps. Particularly good results are obtained when the present yeasts are used in admixture with phytoplanktons and monocell algae since this minimizes the amounts of phytoplanktons which may be utilized. When using as compound feeds for breeding of aquianimals, the compounding ratio of the present yeast to the other components in the feed is usually about 5–10 wt/wt %, based on the total weight. The compounding ratio will be calculated based on the particular kind of fish to be fed. With breeding spawns, the present yeasts may also be used in combination with conventional feeds for use in the initial stage of breeding.

As stated hereinbefore, the present invention is based on a novel technical idea that a culture product of a specific and peculiar yeast is served as a feed for use in the aquianimal cultivation. It is a novel fact found and developed by the present inventors that marine yeasts resistant to sea water or halophilic yeasts are obtained in high yields using a simple culture medium comprising waste molasses and an inorganic nitrogen compound in the major proportion and potassium salt and phosphate in the minor proportion, and that the thus obtained yeasts are extremely useful as feeds in aquianimal cultivation.

The following non-limiting examples are illustrative of the invention.

EXAMPLE 1

One hundred ml. of a sea water medium containing 3 wt/vol % of cane molasses (calculated as sugar), 0.1 wt/vol % of urea, 0.2 wt/vol % of $(NH_4)_2SO_4$ and 0.2 wt/vol % of $KH_2PO_4$ were placed into a SAKAGUCHI shaking flask having a capacity of 500 ml. and sterilized. *Toluropsis famata* (BIKOOKENKINKI No. 350; NRRL Y-7349) having a COD rising index of 110 and an RNA excretion rate of 2.85%, which had been isolated from epidermis of Porphyra tenera collected in the sea along the shore, was then transplanted into this medium and prepropagated at 30°C with shaking for 24 hours. Separately, 10 l. for a sea water medium obtained by dissolving 5.0 wt/vol % of cane molasses (calculated as sugar), 0.2 wt/vol % of urea, 0.4 wt/vol % of KCl and 0.04 wt/vol % of $H_3PO_4$ (85% purity) in a filtered sea water, was placed into a jar fermenter having a capacity of 20 l. and sterilized. 500 milliliters of the seed culture liquor obtained previously was then inoculated into this medium and cultured at 30°C for 20 hours with agitation at a rate of 450 r.p.m. and with aeration at a rate of 100% relative to the volume of the medium, said medium being controlled throughout the culturing to pH 4.5. There was obtained a suspension of the cultured cells (yield of the dried cell: 3.8 g/dl.)

The suspension was centrifuged to separate the cells. After washing twice with sea water, the cells were lyophilized for preservation.

Nauprius of Brine Shrimp (*Artemia salina*), which had been artificially incubated in sea water adjusted to specific gravity of 1.042 by addition of NaCl, were fed with an appropriate amount of the preserved cells to culture the same. The culturing was carried out for 12 days in a breeding medium at pH 8.0, at 27°–28°C and with aeration at a rate of 1 to 2% relative to the medium, said medium being prepared by suspending the aforesaid preserved cells in the medium so that OD value at 610 m$\mu$ of the medium may be maintained constantly at 0.02. An average length of 100 adults, as measured on the 10th day of the culturing, was 14.5 mm. The yield of the plankton thus obtained was 85%.

Using pulp waste liquor yeast (Candida utilis commercially available as Magna Yeast A-3), a control experiment was conducted to culture the Brine Shrimp in the same manner as above. An average length of the adults was found to be 6.4 mm., and the yield of the plankton was 28%.

EXAMPLE 2

A marine yeast, *Torulopsis candida* var. marina (BIKOOKENKINKI No. 346; NRRL Y-7345) having a COD rising index of 124 and an RNA excretion rate of 3.57, which had been isolated from a pulverized product of Shell Shrimp (name in Japanese: YADOKARI), was prepropagated using the same procedure as in Example 1. 10 liters of a sea water medium obtained by dissolving 5 wt/vol % of cane molasses (calculated as sugar), 0.4 wt/vol % of $(NH_4)_2SO_4$, 0.05 wt/vol % of KCl and 0.05 wt/vol % of $H_3PO_4$(85% purity) in a filtered sea water, was charged into a jar fermentor having a capacity of 20 l. and sterilized. One liter of the prepropagation liquor was then inoculated into this medium. The culturing was conducted at 27°–30°C, with agitation at a rate of 450 r.p.m., and with aeration at a rate of 100% relatively to the medium for 3 days. pH value of the medium may be maintained constantly at 5.0. The same sea water medium as mentioned above may be supplied continuously during the course of the culturing and the culture liquor may be collected continuously. There was obtained a large amount of the cell bodies which were then lyophilized for preservation. The yield of the cell bodies as dried was 3.75 g/dl.

The cell bodies thus obtained were mixed with marine chlorella (*Chlorella pyrenoidosa* var. marinae) so as to give a mixture comprising the two in a cell ratio of 5:3. The mixture was continuously poured into a tank having a capacity of 500 l., into which *Brachionus calyciflorus* ("SHIOMIZU TSUBOWAMUSHI", in Japanese) has been charged at a concentration of 50 cell/ml, so that the OD value of the resulting culture liquor was maintained at 0.2. The culturing was continued for 6 days at 22°–25°C and with aeration at a rate of 10% relative to the medium. There was obtained a plankton suspension having a concentration of 580 cell/ml. In control experiments where baker's pressed yeast (*Saccharomycea cerevisiae*) and marine chlorella only were used respectively, the maximum concentrations of the plankton suspensions obtained were 170 cell/ml and 68 cell/ml.

EXAMPLE 3

Using 500 l. of a culturing liquor having the following composition, which had been charged into a 1 cubic meter tank, *Rhodotorula rubra* var. marina (BIKOOKENKINKI No. 348; NRRL Y-7347) having a COD rising index of 131 and an RNA excretion rate of 4.35, which had been isolated from sea water, which had been isolated from sea water, was cultured at 30°C under aeration-agitation. The cells thus obtained were formed into pressed yeast and kept in cold storage for preservation.

The pressed yeast was used as feed for *Mylio macrocephalus* mentioned below. Fry of black porgy, which had grown by means of artifical insemination and incubation to such a degree that they can just be observed visually as becoming turbid after 3 days from the data of incubation, were placed into a 50 l. cultivation tank made of vinyl chloride, to which marine chlorella (*Chlorella pyrenoidosa* var. marinae) accommodated to sea water had been added as an oxygen donor, and fed with the above-mentioned feed for farming. Two hundred fry were picked out from those placed in the water tank and bred in the condition where water temperature was controlled to 20°C. They were fed with the aforesaid pressed yeast in an amount of 100 mg/day together with an excess amount of *Bruschionus calyciflorus* ("SHIOMIZU TSUBOWAMUSHI", in Japanese) from the tenth day after the incubation, and with nauplius incubated artificially with Brine Shrimp from the 25th day thereafter. After 50-days' breeding, an average length of the grown fry was 27.5 mm. and 52 fry out of 200 were left alive. In a control experiment where pressed yeast was used in place of the above-mentioned marine yeast, all the fry died out, and there was a high incidence of gas disease.

| Composition of Culturing Liquor for Marine Yeast | | |
|---|---|---|
| Beet Molasses | 70 g. | (using samples having a sugar content of 55%) |
| $(NH_4)_2SO_4$ | 2 g. | |
| KCl | 200 mg. | |
| $H_3PO_4$ | 0.5 ml. | |
| Sea Water | 1000 ml. | |
| pH | 5.0 | |

During the course of the culturing, the liquor was adjusted to pH 5.0 by addition of ammonia water.

EXAMPLE 4

Following the procedure of Example 1, *Saccharomyces disaccharomellis* (BIKOOKENKINKI No. 347; NRRL Y-7346) with a COD rising index of 108 and an RNA excretion rate of 3.30 which had been isolated from *Ulva pertusa* was cultured and preserved in the form of a pressed yeast. The pressed yeast (moisture content: about 65%) was suspended in sea water so as to give a suspension having a concentration of 10 g/dl. Alginic acid was dissolved in this suspension so as to prepare a solution having a concentration of 4 g/dl. A glass sheet was coated on the surfaces with the solution and immersed into a 10 wt/vol % solution of $CaCl_2$ to obtain an alginic acid filmy feed. Young shells of *Notohaliotis discus* in the sedentary stage, which had been incubated artificially according to ordinary procedure, were fed with the feed. The breeding was carried out using a small amount of running water and in a scale of about 320 shells in average per pannel. After 40 days, the yield of the grown shells was 84%. A control experiment was conducted using baker's pressed yeast in the same procedure as above. On the fifth day of the breeding, young shells began to die, and elution of the cell bodies took place. After 40 days, only 7 shells were left alive out of the whole pannel.

EXAMPLE 5

*Saccharomyces acidosaccharophilli* (BIKOOKENKINKI No. 349; NRRL Y-7348) having a COD rising index of 119 and an RNA excretion rate of 3.14%, which had been cultured and treated in the same manner as in Example 1, was used as a feed for breeding *Brachionus calyciflorus*.

*Brachionus calyciflorus* was placed into a breeding medium so as to give a concentration of 30 cell/ml. The medium charged was charged into a 5 l. cylinder made of vinyl chloride. The feeding was conducted so that the OD value of the medium was maintained constantly at 0.1–0.3. The breeding was carried out at 20°C in average with aeration for 7 days. There was obtained a plankton suspension having a concentration of 570 cell/ml.

A control experiment using baker's pressed yeast was conducted. The maximum concentration of the plankton suspension obtained was 140 cell/ml. After the breeding was over, the COD rising index was measured to show 580, and the RNA excretion rate was found to be 52.41 as reported in Table 1 hereof.

EXAMPLE 6

One liter of a breeding medium prepared by adding chelated metal (trade name, Clewat-32, produced by Teikoku Kagaku Kogyo Co. Ltd., Japan) at a concentration of 0.5 g/l in sea water was placed into a glass circular tube of 12 cm. in diameter. Fry of *Tigriopus japonica* were liberated into the tube in a proportion of 1 fish/ml.

A medium (modified medium of MIN) was prepared by dissolving 1.25 g. of $KNO_3$, 1.25 g. of $KH_2PO_4$, 1.25 g. of $MgSO_4.7H_2O$, 0.02 g. of $FeSO_4.7H_2O$ and 1 ml. of A-5 solution in sea water per 1000 ml. of the water, and adjusting pH to 5.5. The A-5 solution contains 2.86 g. of $H_3BO_3$, 1.81 g. of $MnCl_2.4H_2O$, 0.22 g. of $ZnSO_4.7H_2O$, 0.08 g. of $CuSO_4.5H_2O$ and 0.21 g. of $Na_2MoO_4$ and water is added until the total volume is one liter and then one drop of conc. $H_2SO_4$. Marine chlorella (*Chlorella pyrenoidosa* var. *marinae*) isolated from sea water was transplanted into this medium and cultured on a large scale production of 20°–25°C with aeration at a rate of 2–3% per minute.

A yeast obtained according to the same procedure as in Example 2 was blended with the chlorella cultured above to prepare a relatively concentrated feed liquor having a blending ratio of 3.5 : 1.5 based on dry weight. The breeding was conducted at 22°–24°C with aeration at a rate of 1% per minute, and the fry were fed with the feed liquor so that the OD value of the breeding water was maintained at 0.1–0.2.

On the fourteenth day of the breeding, the propagation rate of Tigriopus was found to be 36 fish/ml. (only imagines). For comparison, the growth rates of Tigriopus observed in a control where only marine yeast was used and a control where only chlorella was used were 21 fish/ml and 3 fish/ml, respectively.

EXAMPLE 7

Fry of *Brachionus rubens* were liberated into 800 liters of exactly the same breeding medium as in Example 2 in a proportion of 500 fry/ml, and the medium was charged into a 1 cubic meter culture tank.

Living cells (in a paste-like form and containing about 70% of water) obtained by centrifuging marine yeast (BIKOOKENKINKI No. 348; NRRL Y-7347) which had been cultured in the same procedure as in Example 1 were mixed in a proportion of 2 : 1 with marine chlorella obtained by culturing and centrifugal separation in the same manner as in Example 6, to prepare a feed.

The fry were fed with the feed at a rate of 500 g/day and bred in a sunny place at the window at 23°–25°C with aeration at a rate of 2% per minute and in such manner that one-half volume of the whole medium was withdrawn (the fry were thinned out accordingly) every day and the remainder was then diluted to two times with a fresh medium each time. Thus, there was obtained over a period of 7 days a highly densed medium with the fry at a proportion of 80–100 fry/ml. every day.

EXAMPLE 8

5 liters of a breeding medium were prepared by adding chelated metal Clewat-32 to sea water in a proportion of 0.5 g/l. and adjusting the specific gravity to 1.042 by addition of common salt, the pH value of said medium being adjusted to 8.2, 2,500 nauplius of Brine Shrimp (*Artemia salina of California origin*), which had previously been incubated, were liberated into this medium.

The nauplii were fed with the same drum dry feed as obtained in Example 4 in such a manner that the OD value of the medium was maintained constantly at 0.2, and bred at 27°–28°C with aeration at a rate of 0.5% per minute. On the tenth day of the breeding, there could be confirmed Brine Shrimp of 4–5 mm in length in a proportion of 41 shrimp/100 ml.

In control experiments with marine yeast alone and with chlorella alone, there were observed Brine Shrimp in proportions of 33 shrimp/100 ml. and 12 shrimp/100 ml.

EXAMPLE 9

Each group consisting of 95,000 nauplii of *Penaeus japonicus* were liberated in 2 tanks each having a capacity of 1 cubic meter and filled with sea water filtered through sand.

In one tank of the two, designated as a compound feed plot, the nauplii were fed with marine yeast obtained according to the same manner as in Example 2 but without the drying treatment, in combination with marine chlorella obtained in the same procedure as in Example 6, at the respective rates of 50 g/day and 15–20 g/day, each feed containing about 70% of water. In the other tank, designated as a marine chlorella plot, they were fed with the marine chlorella alone at a rate of 50 g/day. pH value of the breeding medium in each plot was adjusted with a weak acid to about 8.0. The nauplii were fed additionally with *Brachionus calyciflorus* when they reached the zoea stage, and with Altemia when they reached the mysis or post larva stage. The breeding media were kept at 22°–25°C with aeration at a rate of 2% per minute. The results obtained in both plots are shown in Table 3. As is clear from the table, in the blended feed plot, the yields of the nauplii reaching the stage of mysis and post larva are extremely high and the growth rate thereof very fast, compared with the case of the marine chlorella plot.

Table 3

| Breeding period (day) | Compound feed plot Value determined | | marine chlorella plot Value determined | |
|---|---|---|---|---|
| | Form | Survival rate | Form | Survival rate |
| 1 | Nauplius, 1st stage | 100 % | Nauplius, 1st stage | 100 % |
| 3 | Zoea, 1st stage | 100 % | Zoea, 1st stage | 100 % |
| 5 | Mysis | 98–100% | Zoea, 2-3rd stage | 63–70 % |
| 7 | Post larva | 93 % or higher | Mysis 80 % | 57–65 % |
| 10 | | | Post larva | 50–60 % |

EXAMPLE 10

*Rodotorula marine* IFO 0928 was cultured in the same medium as in Example 1. The yeast cell bodies in a paste-like state were refrigerated for preservation. In exactly the same procedure as in Example 2, *Brachionus calyciflorus* was cultured for 6 days using the preserved yeast as a feed. There was obtained a dense culture liquor having a concentration of 280 cell/ml.

EXAMPLE 11

*Rodotorula texensis* IFO 0932 was cultured in the same medium as in Example 1. The yeast cell bodies thus obtained were washed and then dried in a drum. The dried yeast was blended in a proportion of 5 : 1 with marine chlorella (*Chlorella pyrenoidosa* var. marinae) obtained according to the procedure of Example 6 to prepare a blended feed. Following a similar procedure to that of Example 6, fry of Tigriopus japonicus were fed with the blended feed and bred. On the 18th day, it was confirmed that the imagines had propagated in the proportion of 27 count/ml.

EXAMPLE 12

About 100,000 fry in the zoea stage of *Neptunus trituberculans* ("GAZAMI" in Japanese) were liberated into a circular water tank having a capacity of 1 cubic meter which had been filled with 800 liters of sea water. The fry were fed with a blended feed, which had been prepared by blending marine yeast obtained in the same manner as in Example 2 in equal proportions with a mixture of Chaetocerus and Scenedesmus isolated and obtained from sea water. The fry were fed with *Brachionas calyciflorus* in combination with the blended feed when the fry reached the second stage. The blending ratio and amounts fed employed herein with respect to the marine yeast and the mixture of Chaetocerus and Scenedesmus were the same as in Example 9. The amount of *Brachionas calyflorus*, with which the fry were fed a day, was equivalent to a concentration of 1000–1500 cell/l. The breeding was initiated to start for the first period of about 13 days by keeping the breeding medium at 21°C with aeration at a rate of 2–3% per minute. Thereafter, it was continued by increasing gradually the water temperature of the medium, i.e. at 24°C for 9 days and at 28°C for 7 days. On the 28th day after initiation of the breeding, it was confirmed that 76% of Megalopa fry were still alive.

Simultaneously, a control experiment was effected using chlorella alone as a feed. On the 38th day after the breeding had been initiated, only 21% of Megalopa fry were still alive.

EXAMPLE 13

800 liters of sea water were charged into a circular water tank having a capacity of 1 cubic meter. One species of ultra ship shell in Japan was liberated into this tank in the proportion of 1000 larva/l. and fed with a blended feed in such a manner that the OD value of the breeding medium was maintained constantly at 0.2–0.4. The blended feed had been prepared by blending a paste of marine yeast as in Example 3 in the proportion of 3 : 1 with a culture product obtained by culturing, in a modified medium of MIN as indicated in Example 6, *Chlamydomonus sp.* which had been isolated and obtained from sea water. The breeding medium was maintained at 21°–23°C and adjusted to pH 8.0 or so. On about the 14th day after the breeding had been initiated, the larvae began to move to inhabit the bottom of the tank. On the 18th day, they almost perfectly inhabited the tank bottom. The yield of the larvae was approximately 56% when they were going to move to the tank bottom.

EXAMPLE 14

A mixture was prepared by mixing together 1 kg. of a binder comprising 1 part of carboxymethyl cellulose and 3 parts of wheat flour, 2 kg. of Northernseas white fish meal and 10 g. of Halver's plemix (trade name: "KOKIN PLEMIX"). The mixture was blended with 500 g. of a drum dry product of the marine yeast obtained as in Example 3 and dried in a drum to obtain a blended feed. 8 parts of the blended feed were kneaded with 2 parts of frozen sand eel (*Ammobytes personatus*) to prepare a feed for use in the breeding of *Selioda quinqueradiata* (young yellow-tail) of about 80 cm in length (test plot). Separately, the same blended feed as above was prepared except that 500 g. of magna yeast was used in place of the marine yeast (control plot).

The breeding of *Serioda quinqueradiata* was conducted according to conventional procedures, in a specially made fish preserve having small sections of 3 m × 3 m × 3 m in size. Fry having an average weight of 70 g. were liberated into each section at a proportion of 300 fry/section. In each plot, the fry were fed with the feed in an amount equivalent to 3% of the weight of the fry per day, and the breeding was continued for 90 days.

10 fry each thus bred were randomly selected from each section and tested to determine digestibility and index of increase in weight (i.e. the amount of a feed, in dry weight, required to obtain an increase of 1 kg in weight of the fish). The test results were as follows:

| Plot | Index of Increase in Weight | Digestibility |
|---|---|---|
| Test plot | 1.48 | 84.5% |
| Control plot | 1.95 | 78.1% |

EXAMPLE 15

A concrete cultivation tank having an area of about 5 m² and a capacity of about 3 m³ was filed with spring water from a mountain recess as a breeding medium. 10,000 Ayu-fish fry, which had been artificially incubated, were liberated into this tank. As a feed, there was employed a marine yeast obtained in the same manner as in Example 4, and Brachionus sp. which had been bred by use of limnetic chlorella (*Chlorella ellipsoidea* IAM C-87) cultured in MIN medium indicated in Example 1 but using fresh water in place of the sea water.

On the third day after liberation, the fry were fed with the feed in a proportion of 2000 fry/1/day. On the 10th day, the feed rate was increased to 1000 fry/1/day, and simultaneously, the fry were fed with 4 : 1 mixed ground-bait of the marine yeast and chlorella obtained according to the procedure of Example 1 at a rate of 1 g/day. The feed rate was then gradually increased to 15 g/day from the 15th to 30th day, and thereafter, to about 30 g/day together with Brachionus sp. at a rate of 2000 fry/1/day. The breeding was continued for 60 days. There were confirmed that 6,300 Ayu-fish fry survived and grew to 250–300 mm in length.

During the course of breeding, the breeding medium was kept constantly at 15°–16°C and adjusted to a pH of about 7.0. The OD value thereof was maintained at about 0.2. On and after the 40th day, the capacity of cultivation tank was doubled.

The present method and feed are applicable to zooplanktons, fish, octopus, shells and crustaceans. The zooplanktons include, for example, those belonging to Copepoda selected from genera Calanus, Cyclops, Calocalanus and Oithona, and to Cladocera, Rotatoria and Protozoa selected from genera Daphnia and Monia. The fish are, for instance, of *Plecoglossus altivelis*, *Chrysophry major*, *Amanses modestus*, *Limanda yokohamae*, *Mugil cephalus*, *Sebasticus marmoratus* and *Serioda quinqueraditata*. The crustaceans may be selected from *Neocaridina denticulata*, *Macrobrachium nipponense*, *Penaeus japonicus* and *Penaeus orientalis*. The shells comprise, for example, *Pinctada martensii*, *Anadara broughtonii*, *Tapes japonica*, *Lopha cristagalli* and *Notahaliotis discus*. In addition, algae such as Chlorella, Chlamydomonus, Chaetoceros, Scenedesmus and Ulva are usable in the present invention.

What is claimed is:

1. A method of aquianimal cultivation which comprises feeding the aquianimal with cells obtained by aerobically culturing in a sea water medium containing waste molasses and an inorganic nitrogen compound as the sources of carbon and nitrogen, a yeast strain selected from the group consisting of
NRRL Y-7345
NRRL Y-7346
NRRL Y-7347
NRRL Y-7348 and
NNRL Y-7349

2. A method according to claim 1, wherein as the aquianimal, there are used a zooplankton of species Copepoda selected from the group consisting of genera Calanus, Cyclops, Calocalanus and Oithona, and of species Cladocera, *Rotatoria* and *Protozoa* selected from the group consisting of genera Daphnia and Monia.

3. A method according to claim 1, wherein as the aquianimal, there are used fish and octopuses selected from the group consisting of *Phecoglossus altivelis*, *Chrysophry major*, *Amanses modestus*, *Limanda yokohamae*, *Mugil cephalus*, *Sebasticus marmoratus* and *Serioda quinqueradiata*.

4. A method according to claim 1, wherein as the aquianimal, there are used crustaceaus selected from the group consisting of species *Neocaridina denticulata*, *Macrobrachium nipponense*, *Penaeus japonicus* and *Penaeus orientalis*.

5. A method according to claim 1, wherein as the aquianimal, there are used shells selected from the group consisting of species *Pinctada, martensii*, *Anadara broughtonii*, *Tapes japonica*, *Lopha cristagalli* and *Notahaliotis discus*.

6. A method according to claim 1 wherein waste molasses and an inorganic nitrogen compound are used as the sole sources of carbon and nitrogen.

7. A method according to claim 1, wherein as the algae, there are used algae selected from the group consisting of genera Chlorella, Chlamydomonus, Chaetoceros, Scenedesmus and Ulva.

8. A method according to claim 1, wherein as the aquianimal, there are used a zooplankton of species Copepoda selected from the group consisting of genera Calanus, Cyclops, Calocalanus and Oithona, and of species *Cladocera*, *Rotatoria* and *Protogoa* selected from the group consisting of genera Daphnia and Maina.

9. A method according to claim 1, wherein as the aquianimal, there are used fish and octopuses selected from the group consisting of *Plecoglossus altiveli*, *Chrysophy major, Amanses modestus, Limanda yokohamae, Mugil cephalus, Sebasticus marmoratus* and *Serioda quinqueradiata*.

10. A method according to claim 1, wherein as the aquianimal, there are used crustaceans selected from the group consisting of *Neocaridina denticulata, Macrobrachium nipponense, Penaeus japonicus* and *Penaeus orientalis*.

11. A method according to claim 1, wherein as the aquianimal, there are used shells selected from the group consisting of *Pinctada martensii, Anadara broughtonii, Tapes japonica, Lopha cristagalli* and *Notahaliotis discus*.

12. A method according to claim 1, wherein waste molasses and an inorganic nitrogen compound are used as the sole sources of carbon and nitrogen.

13. A method of aquianimal cultivation which comprises feeding the aquianimal with cells and algae, said cells being recovered from a culture obtained by aerobically culturing in a sea water medium containing waste molasses and an inorganic nitrogen compound as the sources of carbon and nitrogen respectively, a yeast strain selected from the group consisting of
NRRL Y-7345
NRRL Y-7346

NRRL Y-7347
NRRL Y-7348 and

NRRL Y-7349

* * * * *